United States Patent
Helenek et al.

(10) Patent No.: US 6,960,571 B2
(45) Date of Patent: Nov. 1, 2005

(54) METHODS AND COMPOSITIONS FOR ADMINISTRATION OF IRON FOR THE TREATMENT OF RESTLESS LEG SYNDROME

(75) Inventors: Mary Jane Helenek, Brookville, NY (US); Ralf A. Lange, Amagansett, NY (US); Fred B. Oldham, West Chester, PA (US); Marc L. Tokars, Douglassville, PA (US)

(73) Assignee: Luitpold Pharmaceuticals, Inc., Shirley, NY (US)

(*) Notice: Subject to any disclaimer, the term of this patent is extended or adjusted under 35 U.S.C. 154(b) by 0 days.

(21) Appl. No.: 10/389,228

(22) Filed: Mar. 14, 2003

(65) Prior Publication Data

US 2004/0180849 A1 Sep. 16, 2004

(51) Int. Cl.[7] .................. A61K 31/7012; A61K 31/555
(52) U.S. Cl. .................. 514/53; 514/184; 514/483; 514/365; 514/387; 514/547; 514/674; 514/23; 514/58; 514/59; 514/502; 536/4.1; 424/489; 424/733; 424/9
(58) Field of Search .................. 514/53, 184, 483, 514/365, 367, 547, 674, 23, 58, 59, 502; 536/4.1; 424/489, 733, 9

(56) References Cited

U.S. PATENT DOCUMENTS

| | | | |
|---|---|---|---|
| 4,827,945 A | | 5/1989 | Groman et al. |
| 5,248,492 A | | 9/1993 | Groman et al. |
| 5,700,832 A | * | 12/1997 | Baik et al. .................. 514/502 |
| 6,611,707 B1 | * | 8/2003 | Prausnitz et al. .............. 604/21 |

FOREIGN PATENT DOCUMENTS

| WO | WO 00/25821 | 5/2000 |
|---|---|---|
| WO | WO 01/74162 | 10/2001 |

OTHER PUBLICATIONS

Earley et al. "Abnormalities in CSF concentrations of ferritin and transferrin in restless legs syndrome." Neurology, 54, pp. 1698–1700, Apr. (2 of 2) 2000.*

Allen et al., "MRI Measurement of Brain Iron in Patients with Restless Legs Syndrome," Neurology, 2001, pp. 263–265, vol. 56.

Allen et al., "Augmentation of the Restless Legs Syndrome with Carbidopa/Levodopa," Sleep, 1996, pp. 205–213, vol. 19.

Allen et al., "Restless Legs Syndrome: A Review of Clinical and Pathophysiologic Features," J. Clin. Neurophysiol., 2001, pp. 128–147, vol. 18.

Allen et al., "Validation of the Johns Hopkins Restless Legs Severity Scale," Sleep Medicine, 2001, pp. 239–242, vol. 2.

Bailie et al., "Restless Legs Syndrome—Focus on Dopaminergic Agents," Med Facts, 2001, vol. 3, 1 page, obtained from http://www.nephrologypharmacy.com/downloads/Medfacts3–1.pdf.

Ben–Shachar et al., "Effect of Iron Chelators on Dopamine D2 Receptors," J. Neurochem., 1985, pp. 999–1005, vol. 45.

Bonnet et al., "ASDA Report, Atlas and Scoring Rules," Sleep, 1993, pp. 748–759, vol. 16.

Breuer et al., "A Fluorescence–Based One–Step Assay for Serum Non–Transferrin–Bound Iron," Anal. Biochem., 2001, pp. 194–202, vol. 299.

(Continued)

Primary Examiner—James O. Wilson
Assistant Examiner—Devesh Khare
(74) Attorney, Agent, or Firm—Sonnenschein Nath & Rosenthal LLP (57) ABSTRACT

A method of treating Restless Leg Syndrome, includes administering to a subject an iron complex having an iron release rate greater than IDI. The iron release rate is determined at a concentration of at least 2,000 µg/dl.

16 Claims, 1 Drawing Sheet

OTHER PUBLICATIONS

Chesson et al., "Practice Parameters for the Treatment of Restless Legs Syndrome and Periodic Limb Movement Disorder, An American Academy of Sleep Medicine Report, Standards of Practice Committee of the American Academy of Sleep Medicine," Sleep, 1999, pp. 961–968, vol. 22.

Conrad et al., "Iron Absorption and Transport," Am. J. Med. Sci., 1999, pp. 213–229, vol. 318.

Danielson et al., "Pharmacokinetics of Iron(III_–Hydroxide Sucrose Complex After a Single Intravenous Dose in Healthy Volunteers," Arzneimittelforschung, 1996, pp. 615–621, vol. 46.

Davis et al., "A Randomized, Double–Blind Placebo–Controlled Trial of Iron in Restless Legs Syndrome," European Neurology, 2000, pp. 70–75, vol. 43.

Earley et al., "Pergolide and Carbidopa/Levodopa Treatment of the Restless Legs Syndrome and Periodic Leg Movements in Sleep in a Consecutive Series of Patients," Sleep, 1996, pp. 801–810, vol. 19.

Earley et al., "Abnormalities in CFS Concentrations of Ferritin and Transferrin in Restless Legs Syndrome," Neurology, 2000, pp. 1698–1700, vol. 54.

Earley et al., "Randomized, Double–Blind, Placebo–Controlled Trial of Pergolide in Restless Legs Syndrome," Neurology, 1998, pp. 1599–1602, vol. 51.

Ekbom, "Restless Legs Syndrome," Neurology, 1960, pp. 868–873, vol. 10.

Ekbom, "Restless Legs Syndrome," Focus on Dopaminergic Agents, Med Facts, 2001, pp. 868–873, vol. 3.

Erikson et al., "Iron Deficiency Alters Dopamine Transporter Functioning in Rat Striatum," J. Nutr., 2000, pp. 2831–2837, vol. 130.

Esposito et al., "Labile Iron in Parenteral Iron Formulations and its Potential for Generating Plasma Nontransferrin-Bound Iron in Dialysis Patients," Eur. J. Clin. Invest., 2002, pp. 42–49, vol. 32.

Fishbane et al., "The Safety of Intravenous Iron Dextran in Hemodialysis Patients," Am. J. Kidney Dis., 1996, pp. 529–534, vol. 28.

Geisser et al., "Structure/Histotoxicity Relationship of Parenteral Iron Preparations," Arzneimittelforschung, 1992, pp. 1439–1452, vol. 42.

Gelman et al., "MR Imaging of Human Brain at 3.0 T: Preliminary Report on Transverse Relaxation Rates and Relation to Estimated Iron Content," Radiology, 1999, pp. 759–767, vol. 210.

Gorny et al., "Evaluation of the PAM–RL System for the Detection of Periodic Leg Movements During Sleep in the Lab and Home Environments," Sleep, 1986, p. 183, vol. 21.

Hamstra et al., "Intravenous Iron Dextran in Clinical Medicine," JAMA, 1980, pp. 1726–1731, vol. 243.

Hening et al., "Dyskinesias While Awake and Periodic Movements in Sleep in Restless Legs Syndrome: Treatment with Opoids," Neurology, 1986, pp. 1361–1366, vol. 36.

Hening et al., "The Treatment of Restless Legs Syndrome and Periodic Limb Movement Disorder, An American Academy of Sleep Medicine Review," Sleep, 1999, pp. 970–999, vol. 22.

Jacobs et al., "Colorimetry and Constant–Potential Coulometry Determinations of Transferrin–Bound Iron, Total Iron-Binding Capacity, and Total Iron in Serum Containing Iron–Dextran, with Use of Sodium Dithionite and Alumina Columns," Clin. Chem., 1990, pp. 1803–1807, vol. 36.

Montplaisir et al., "Restless Legs Syndrome and periodic Movements in Sleep: Physiopathology and Treatment with L–dopa," Clin. Neuropharmacol., 1986, pp. 456–463, vol. 9.

Montplaisir et al., "Immobilization Tests and Periodic Leg Movements in Sleep for the Diagnosis of Restless Leg Syndrome," Mov. Disord., 1998, pp. 324–329, vol. 13.

Montplaisir et al, "Restless Legs Syndrome and Periodic Leg Movements in Sleep: The Primary Role of Dopaminergic Mechanism," Eur. Neurol., 1991, pp. 41–43, vol. 31.

Nelson et al., "In vivo Dopamine Metabolism is Altered in Iron–Deficient Anemic Rats," J. Nutr., 1997, pp. 2282–2288, vol. 127.

Nordlander, "Therapy in Restless Legs," Acta Medica Scandinavica, 1953, pp. 453–457, vol. 145.

O'Keeffe et al., "Iron Status and Restless Legs Syndrome in the Elderly," Age Ageing, 1994, pp. 200–203, vol. 23 (and abstract only from http://ageing.oupjournals.org/cgi/content/abstract/23/200).

Pelletier et al., "Sensory and Motor Components of the Restless Legs Syndrome," Neurology, 1992, pp. 1663–1666, vol. 42.

Pollmacher et al., "Periodic Leg Movements (PLM): Their Relationship to Sleep Stages," Sleep, 1993, pp. 572–577, vol. 16.

Silber et al., "Pergolide in the Management of Restless Legs Syndrome: An Extended Study," Sleep, 1997, pp. 878–882, vol. 20.

Simon, "Anemia," http://www.healthandage.com/html/well_connected/pdf/doc57.pdf, 17 pages, 2003.

Staedt et al., "Nocturnal Myoclonus Syndrome (Periodic Movements in Sleep) Related to Central Dopamine D2–Receptor Alteration," Eur. Arch. Psychiatry Clin. Neurosci., 1995, pp. 8–10, vol. 245.

Sun et al., "Iron and the Restless Legs Syndrome," Sleep, 1998, pp. 381–387, vol. 21.

Turjanski et al., "Striatal Dopaminergic Function in Restless Legs Syndrome: 18F–dopa and 11C–raclopride PET Studies," Neurology, 1999, pp. 932–937, vol. 52.

Ward et al., "Brain Iron in the Ferrocene–Loaded Rat: Its Chelation and Influence on Dopamine Metabolism," Biochem. Pharmacol., 1995, pp. 1821–1826, vol. 49.

RLS–QLI Restless Legs Syndrome–Quality of Life Instrument; RLS–QLI © RLS Foundation, May 1, 2002.

SF–12 Health Survey, Protocol PPXAPD–0072–138, Final Jan. 22, 2002.

* cited by examiner

Fig. 1

METHODS AND COMPOSITIONS FOR ADMINISTRATION OF IRON FOR THE TREATMENT OF RESTLESS LEG SYNDROME

BACKGROUND

Restless Legs Syndrome

Victims seriously afflicted with Restless Leg Syndrome (RLS; also known as Ekbom's syndrome), are virtually unable to remain seated or even to stand still. Activities that require maintaining motor rest and limited cognitive stimulation, such as transportation (car, plane, train, etc.) or attending longer meetings, lectures, movies or other performances, become difficult if not impossible. Tortured by these sensations which become more severe at night, RLS patients find sleep to be virtually impossible, adding to the diminishing quality of their lives. The urge to move, which increases over periods of rest, can be completely dissipated by movement, such as walking. However, once movement ceases, symptoms return with increased intensity. If an RLS patient is forced to lie still, symptoms will continue to build like a loaded spring and, eventually, the legs will involuntary move, relieving symptoms immediately. Rhythmic or semi-rhythmic movements of the legs are observed if the patient attempts to remain laying down (Pollmacher and Schulz 1993). These movements are referred to as dyskinesias-while-awake (DWA) (Hening et al. 1986) or more commonly, periodic limb movements while awake (PLMW).

Clinically, RLS is indicated when four diagnostic criteria are met: (1) a sensation of an urge to move the limbs (usually the legs); (2) motor restlessness to reduce sensations; (3) when at rest, symptoms return or worsen; and (4) marked circadian variation in occurrence or severity of RLS symptoms; that is, symptoms worsen in the evening and at night (Allen and Earley 2001a). First recognized by Willis in 1685, RLS has been misunderstood and confused with periodic limb movements in sleep (PLMS; which may be a part of RLS, but does not define RLS), periodic limb movement disorder (PLMD; a sleep disorder) and nocturnal (or sleep) myoclonus (Allen and Earley 2001a).

Iron and Dopamine Concentrations are Intertwined Factors in RLS

Lack of iron and reduced dopamine synthesis in the brain are important factors in RLS (Ekbom 1960, Nordlander 1953). Dopamine is a neural transmitter synthesized in the brain that is essential for proper central nervous system (CNS) function. In the synthesis of dopamine, iron is a cofactor for the enzyme tyrosine hydroxylase, which is the rate-limiting step in dopamine metabolism (Cooper et al. 1991). Iron in the dopaminergic system appears to be an important component in RLS pathophysiology (Chesson A L et al. 1999, Ekbom 1960, Hening et al. 1999, Montplaisir et al. 1991).

Because iron is a co-factor for tyrosine hydroxylase in dopamine synthesis, dopamine is reduced. When chelators (substances that bind metals such as iron, and make them physiologically unavailable) are administered to rats having excessive brain iron, they were effective in reducing dopamine and dopamine turnover (Ward et al. 1995). Studies in iron-deficient animals have also demonstrated decreases in dopamine receptors (Ben-Shachar et al. 1985, Ward et al. 1995), dopamine transporter function and receptor density with an elevation in extracellular dopamine (Erikson et al. 2000, Nelson et al. 1997). These observations in rats are also observed in RLS patients. For example, a decrease in dopamine receptors has been observed in basal ganglia (Staedt et al. 1995, Turjanski et al. 1999). RLS patients have 65% less cerebral spinal fluid (CFS) ferritin (an important iron storage protein) and three-fold more CSF transferrin (iron transport protein in blood and body fluids), despite normal serum levels of ferritin and transferrin in both RLS and controls (Earley et al. 2000). Iron concentrations vary throughout the brain; RLS patients have less iron in the substantia nigra and in the putamen parts of the brain, both sites of dopamine synthesis (Allen et al 2001). In general, decreased ferritin levels are indicative of RLS severity (O'Keeffe et al. 1994, Sun et al. 1998). These observations indicate that the ability of the brain to transport or store iron is abnormal in idiopathic RLS (RLS having no apparent cause)

TABLE 1

Side effects of current treatments for Restless Legs Syndrome (RLS)[1]

| Medication | Disease[2] | Side effects | % affected[3] |
|---|---|---|---|
| levodopa/carbidopa | Parkinson | dyskinesia (inability to control movements), nausea, hallucinations | 4–17 |
| Pergolide w/ levodopa/carbidopa | Parkinson | dyskinesia, nausea, hallucinations, rhinitis (mucous membrane inflammation), constipation, pain | 7–62 |
| Pramipexole | Parkinson | somnolence, insomnia, nausea, constipation, hallucinations | 9–28 |
| Narcotic analgesics | Pain control | respiratory depression, nausea, somnolence, pruritus (severe itching), constipation, urinary retention | none reported |
| Clonazepam | Epilepsy | somnolence, depression, in-coordination | 6–37 |
| Triazolam | Insomnia | drowsiness, dizziness, memory impairment | 1–14 |
| Gabapentin | Epilepsy | fatigue, dizziness, somnolence, ataxia (unable to coordinate muscular movement) | 11–19 |
| Carbamazepine | Epilepsy | fetal malformation, rash, hyponatremia (blood sodium deficiency), hepatotoxicity, blood disorders, ataxia, gastro-intestinal problems, sexual dysfunction, toxicity | 1–33 |
| Clonidine | Hypertension | reduced blood pressure, dermatitis, systemic side effects (dry mouth, somnolence, dizziness, headache) | 8–89 |

TABLE 1-continued

Side effects of current treatments for Restless Legs Syndrome (RLS)[1]

| Medication | Disease[2] | Side effects | % affected[3] |
| --- | --- | --- | --- |
| intravenous iron dextran | iron deficiencies (Fishbane et al. 1996) and random sampling (Hamstra et al. 1980) | anaphylaxis, possibility resulting in death | 0.3–1.7 (Fishbane et al. 1996, Hamstra et al. 1980) |

[1]Table derived from (Chesson AL et al. 1999), except for intravenous iron dextran.
[2]Studies were performed on patients suffering from the indicated disease, not RLS, with the indicated drug.
[3]As reported in the studies referenced within (Chesson AL et al. 1999). See Chesson et al. 1999 for more information. The percent (&) range is derived from the reported percentages for each side effect; thus in the first example, 12–17% suffered from dyskinesia, 6% from nausea and 4% from hallucinations; the reported range is 4–17%.

Treating RLS

Current treatments for RLS are varied and plagued with undesirable side effects (see Table 1). Therapies have included the administration of dopamine agonists (substances that promote the production of dopamine), other dopaminergic agents, benzodiazepines, opiates and anti-convulsants. In cases where RLS results from a secondary condition, such as pregnancy, end-stage renal disease, erythropoietin (EPO) treatment and iron deficiency, removing the condition, such as giving birth or treating with traditional iron supplementation, can reduce or eliminate symptoms in at least some cases (Allen and Earley 2001a). However, RLS resulting from non-secondary conditions "idiopathic" RLS), presents a greater treatment challenge.

Dopaminergic agents such as levodopa generally provide effective initial treatment, but with continued use, tolerance and symptom augmentation occur in about 80% of RLS patients (Allen and Earley 1996); this complication is also common for dopamine agonists (Earley and Allen 1996, Silber et al 1997). The other alternatives, benzodiazepines, opiates and anti-convulsants are not as uniformly effective as the dopamine agents (Chesson AL et al. 1999, Hening et al. 1999). Despite changes in ther treatment regimes, 15–20% of patients find that all medications are inadequate because of adverse effects and limited treatment benefit (Earley and Allen 1996).

Because of the link between iron and dopamine synthesis, iron administration would appear to be a simple and safe treatment to increase body iron stores. An obvious choice is oral administration of iron since such administration is simple and inexpensive. In fact, RLS patients with iron deficiency respond dramatically to oral iron supplements (Ekbom 1960, O'Keeffe et al. 1994). However, in RLS patients with normal serum ferritin levels, the benefits of oral iron therapy decrease inversely to baseline serum ferritin levels: the higher the ferritin at the time of initiating therapy, the less pronounced the benefits (O'Keeffe et al. 1994). This approach to raise body stores of iron is ineffective because the intestinal epithelium controls iron absorption, responding not to dopamine synthesis cues, but to serum iron levels (Conrad et al. 1999). Therefore, oral doses of iron are ineffective, and not tolerated. To increase body stores of iron when serum ferritin levels are normal, methods that bypass intestinal epithelial regulation would need to be used. For example, in the anemia of chronic disease, iron absorption and transport is dramatically impaired and serum ferritin levels being elevated does not accurately reflect stored iron levels in the body. Also in the anemia of chronic disease the only effective way to deliver adequate iron for erythropoiesis to a deprived system is by intervenus administration.

Intravenous administration of iron circumvents the problems and ineffectiveness of orally-administered iron for those RLS patients with normal serum ferritin levels. In fact, intravenous administration of iron dextran solutions, such as INFeD® (Watson Pharma, Inc.; Corona, Calif. (having an average apparent molecular weight of 165,000 g/mole with a range of approximately±10%), and Dexferrum® (American Regent Inc., Shirley, N.Y.) (referred to collectively as "IDI") successfully treats RLS. However, the dosage is high—1000 mg/administration; or about two- to ten-fold more than the usual dose when used to treat other conditions. While IDI offers hope to some RLS patients, it also suffers from significant disadvantages: not only is the dosage high, but also dextran causes anaphylaxis in about 1.7% of the population (Fishbane et al. 1996), a life threatening condition; just less than 50% or those suffering anaphylaxis die.

SUMMARY

In a first aspect, the present invention is a method of treating Restless Leg Syndrome, comprising administering to a subject an iron complex having an iron release rate greater than IDI. The iron release rate is determined at a concentration of at least 2,000 $\mu$g/dl.

In a second aspect, the present invention is a method of treating Restless Leg Syndrome, comprising administering to a subject an iron complex having an iron release rate of at least 115 $\mu$g/dl at a concentration of 3438 $\mu$g/dl by the alumina column test.

In a third aspect, the present invention is a method of treating Restless Leg Syndrome, including administering IDI, the improvement comprising replacing IDI with an iron complex having a greater release rate than IDI.

In a fourth aspect, the present invention is a kit, comprising an iron complex composition having a release rate greater than IDI, a syringe, and a needle for the syringe. The iron release rate is determined at a concentration of at least 2,000 $\mu$g/dl.

DETAILED DESCRIPTION

The present invention makes use of the discovery that an iron complex, having a higher release rate of iron than IDI, has the same effect for the treatment of RLS as IDI, at a lower dosage. These iron complexes avoid the risks of anaphylaxis associated with IDI when administered intravenously due to antibodies against the dextran moiety not being present in other iron complexes and, because of the higher release rate, therapadic dosage can be lowered.

An example of such an iron complex is Venofer® (iron sucrose injection USP), an iron sucrose complex that has an incidence of anaphylactoid reactions of 0.0046% (that is, 1 out of 20,000 people; IDI has a rate of anaphylaxis of 1.7%, or almost 2 out of 100 people). However, any iron complex that has a release rate greater than that of IDI is an effective RLS therapeutic.

Iron Compositions for the Treatment of RLS

Iron complexes are compounds which contain iron in (II) or (III) oxidation state, complexed with an organic compound. These include iron polymer complexes, iron carbohydrate complexes, and iron aminoglycosan complexes. These complexes are commercially available, or have well known syntheses (see, for example, (Andreasen and Christensen 2001, Andreasen and Christensen 2001, Geisser et al. 1992, Groman and Josephson 1990, Groman et al. 1989)).

Examples of iron carbohydrate complexes include iron simple saccharide complexes, iron oligosaccharide complexes, and iron polysaccharide complexes, such as: iron sucrose, iron polyisomaltose (iron dextran), iron polymaltose (iron dextrin), iron gluconate, iron sorbital, iron hydrogenated dextran, which may be further complexed with other compounds, such as sorbital, citric acid and gluconic acid (for example iron dextrin-sorbitol-citric acid complex and iron sucrose-gluconic acid complex), and mixtures thereof.

Examples of iron aminoglycosan complexes include iron chondroitin sulfate, iron dermatin sulfate, iron keratan sulfate, which may be further complexed with other compounds and mixtures thereof.

Examples of iron polymer complexes include iron hyaluronic acid complex, iron protein complexes, and mixtures thereof. Iron protein complexes include ferritin, transferritin, as well as ferritin or transferritin with amino acid substitutions, and mixtures thereof. Preferably, the iron complexes have a molecular mass of at least 30,000, more preferably of 30,000 to 100,000 as determined by HPLC/CPG (as described in Geisser et al 1992). Preferably, the iron complexes have a size of at most 0.1 micrometer, more preferably 0.035 to 0.1 micrometer, as determined by filtration.

The most preferred iron complex is iron sucrose (iron sucrose injection USP, Venofer®). This composition also avoids toxicity issues that are associated with smaller sugars, especially gluconates, which have high iron release rates. Iron sucrose compositions balance these toxicity issues with optimal iron release rates.

Determining Iron Complex Iron Release Rates

The methods of the invention take advantage of the discovery that iron complexes having higher release rates of iron than IDI can be effectively administered at lower doses. IDI has an iron release rate of 69.5–113.5 $\mu$g/dl. In the present invention, the iron complex must have a release rate of at least 115 $\mu$g/dl at a concentration of at least 2000 $\mu$g/dl; including 2000, 3000, 3500, 5000, and 10,000 $\mu$g/dl. Preferably, at least 120 $\mu$g/dl, more preferably, at least 140 $\mu$g/dl. Two tests can be implemented to determine iron release rates, that by Esposito et al. (2000) and by Jacobs et al. (1990).

"Chelator Test" (Esposito et al 2000)

The release rate of a candidate iron complex is the ability of the candidate complex to donate iron to apotransferrin or to an iron chelator, such as desferrioxamine. To detect such transfer, the probes fluorescein-transferrin (Fl-Tf) and fluorescein-desferrioxamine (Fl-DFO) can be used, which undergo quenching upon binding to iron (Breuer and Cabantchik 2001). In short, the method involves mobilization of iron from serum with 10 mM oxalate and its transfer to the metallosensor fluoresceinated apotransferrin (Fl-aTf). Gallium is present in the assay to prevent the binding of labile plasma iron to the unlabelled apotransferrin in the sample. Labile plasma iron values are derived from the magnitude of quenching of the fluorescence signal of fluoresceinated apotransferrin. Fluorescence may be measured using, for example, 96-well plates and a plate reader operating at 485/538 nm excitation/emission filter pair (gain=25).

"Alumina Column Test" (Jacobs et al. 1990)

In this test, samples (serum and candidate iron composition) are passed over an alumina column to absorb organic and drug-bound iron, the elutants are then collected and reconstituted to a pre-selected volume (e.g., 1.5 ml), and the final iron concentration determined using a chemistry analyzer, such as a Hitachi 717 chemistry analyzer. Ferrozine reagents are used, which included detergent, buffers of citric acid and thiourea, ascorbate, and ferrozine. This test is a non-proteinizing method in which detergent clarifies lipemic samples, buffers lower the pH to <2.0 to free iron as $Fe^{3+}$ from transferrin, ascorbate reduces $Fe^{3+}$ to $Fe^{2+}$, and ferrozine reacts with $Fe^{2+}$ to form a colored complex measured spectophotometrically at 560 nm. From this result the value of a control (blank) sample is subtracted from the experimental sample readings, and the results are recorded as the $\Delta$ Tf-bound iron ($\mu$g/dl).

Pharmaceutical Compositions

In many cases, the iron complex may be delivered as a simple composition comprising the iron complex and the buffer in which it is dissolved. However, other products may be added, if desired, to maximize iron delivery, preservation, or to optimize a particular method of delivery.

A "pharmaceutically acceptable carrier" includes any and all solvents, dispersion media, coatings, antibacterial and anti-fungal agents, isotonic and absorption delaying agents, and the like, compatible with pharmaceutical administration (Gennaro 2000). Preferred examples of such carriers or diluents include, but are not limited to, water, saline, Ringer's Lactate solutions and dextrose solution. Supplementary active compounds can also be incorporated into the compositions. For intravenous administration, Venofer® is preferably diluted in normal saline to approximately 2–5 mg/ml. The volume of the pharmaceutical solution is based on the safe volume for the individual patient, as determined by a medical professional General Considerations A iron complex composition of the invention for administration is formulated to be compatible with the intended route of administration, such as intravenous injection. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methylparabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. Preparations can be enclosed in ampules, disposable syringes or multiple dose vials made of glass or plastic.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL™ (BASF; Parsippany, N.J.) or phosphate buffered saline (PBS). The composition must be sterile and should be fluid so as to be administered using a syringe. Such compositions should be stable during manufacture and storage and must be preserved against contamination from microorganisms, such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, benzyl alcohol, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin.

Sterile injectable solutions can be prepared by incorporating an iron complex in the required amount in an appropriate solvent with a single or combination of ingredients as required, followed by sterilization. Methods of preparation of sterile solids for the preparation of sterile injectable solutions include vacuum drying and freeze-drying to yield a solid containing the iron complex and any other desired ingredient.

Systemic Administration

Systemic administration can be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

Carriers

Active compounds may be prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

Kits for Pharmaceutical Compositions

Iron complex compositions can be included in a kit, container, pack or dispenser, together with instructions for administration. When the invention is supplied as a kit, the different components of the composition may be packaged in separate containers, such as ampules or vials, and admixed immediately before use. Such packaging of the components separately may permit long-term storage without losing the activity of the components.

Kits may also include reagents in separate containers that facilitate the execution of a specific test, such as diagnostic tests.

Containers or Vessels

The reagents included in kits can be supplied in containers of any sort such that the life of the different components are preserved and are not adsorbed or altered by the materials of the container. For example, sealed glass ampules or vials may contain lyophilized iron complex or buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that, upon removal, permits the components to mix. Removable membranes may be glass, plastic, rubber, etc.

Instructional Materials

Kits may also be supplied with instructional materials. Instructions may be printed on paper or other substrate, and/or may be supplied on an electronic-readable medium, such as a floppy disc, CD-ROM, DVD-ROM, mini-disc, SACD, Zip disc, videotape, audio tape, etc. Detailed instructions may not be physically associated with the kit; instead, a user may be directed to an internet web site specified by the manufacturer or distributor of the kit, or supplied as electronic mail.

Methods for the Treatment of RLS with Compositions Having Greater Iron Release Rates than IDI Methods of treatment of RLS with iron complex compositions having greater iron release rates than IDI comprise the administration of the complex, either as doses administered over pre-determined time intervals or in response to the appearance and reappearance of RLS symptoms. In general, dosage depends on the route of administration. The preferred route of administration is intravenous infusion; however, certain iron compounds may be administered intramuscularly such as iron dextran. However, any route is acceptable as long as iron from the iron complex is quickly released (more quickly than IDI administered intravenously) such that RLS symptoms are treated.

An appropriate dosage level will generally be about 10 mg to 1000 mg of elemental iron per dose, which can be administered in single or multiple doses, particularly at least 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, 1000.0, and 2000.0 milligrams of elemental iron, and furthermore up to the maximal tolerated dose (MTD) per administration. Preferably, the dosage level will be about 0.1 to about 1000 mg per dose; most preferably about 100 mg to about 500 mg per dose. The compounds may be administered on various regimes (see Example 3).

For example, a 1000 mg of elemental iron of an injectable intravenous iron sucrose complex (Venofer®) is given as a single dose (as a 1.5–5 mg iron/ml in normal saline) to RLS patients. A single intravenous treatment will provide relief of symptoms for an extended period of time, approximately two to twelve months (Nordlander 1953), although relief may be granted for shorter or longer periods. If desired, post-infusion changes in CNS iron status can be monitored using measurements of CSF ferritin (and other iron-related proteins) and of brain iron stores using MRI. Post-infusion changes in RLS are assessed using standard subjective (e.g., patient diary, rating scale) and objective (e.g., P50, SIT, Leg Activity Meters) measures of clinical status. If desired, to better evaluate RLS symptom amelioration, CSF and serum iron values, MRI measures of brain iron and full clinical evaluations with sleep and immobilization tests are obtained prior to treatment, approximately two weeks after treatment, and again twelve months later or when symptoms return. Clinical ratings, Leg Activity Meter recordings and serum ferritin are obtained monthly after treatment. CSF ferritin changes can also be used to assess symptom dissipation. More details are provided in Example 2 and the references cited therein.

The frequency of dosing depends on the response of each individual patient and the administered amount of elemental iron. An appropriate regime of dosing will be once every week to once every eighteen months, more preferably once every two to twelve months, or any interval between, such as once every two months and one day, three, four, five, six, seven, eight, nine, ten and eleven months. Alternatively, the iron complexes may be administered ad hoc, that is, as symptoms reappear, as long as safety precautions are regarded as practiced by medical professionals.

It will be understood, however, that the specific dose and frequency of administration for any particular patient may be varied and depends upon a variety of factors, including the activity of the employed iron complex, the metabolic stability and length of action of that complex, the age, body weight, general health, sex, diet, mode and time of administration, rate of excretion, drug combination, the severity of the particular condition, and the host undergoing therapy.

EXAMPLES

The following examples are provided to illustrate the invention. Those skilled in the art can readily make insignificant variations in the compositions and methods of this invention. The examples are not meant to limit the invention in any way.

Example 1

Iron Release Rates

Intravenous iron agents donate iron to transferrin indirectly through prior intracellular uptake, processing and controlled release. However, evidence that many adverse reactions to intravenous iron agents are dose-related, dose-limiting and vary by class of agent support the hypothesis that direct donation may also occur. Intravenous iron administration at sufficient doses may transiently over-saturate iron binding capacity, and that agents may vary in their potential to donate iron directly.

The ability of candidate iron complexes (intravenous injection preparations for ferric gluconate (also known as sodium ferric gluconate complex in sucrose, Ferrlecit®)), iron sucrose (iron sucrose injection USP, Venofer®) and both available formulations of iron dextran (INFeD® and Dexferrum®) to donate iron to transferrin in serum in vitro was assayed. A series of dilutions of the iron agents were added to fresh serum, passed over an alumina column to remove iron-sugar complexes, and the resulting elutant assayed for transferrin-bound iron.

This assay reliably excludes both iron agent and inorganic iron from interfering with the colorimetric assay of transferrin-bound iron in serum (Jacobs and Alexander 1990).

Parenteral Iron Formulations

Ferric gluconate complex in sucrose, Ferrlecit®, 12.5 mg/ml in 5 ml ampules (Watson Pharmaceuticals, Inc, Corona, Calif.), iron sucrose (iron sucrose injection USP, Venofer®, 20 mg/ml in 5 ml vials; American Regent Inc., Shirley, N.Y.) and two formulations of iron dextran (INFeD®; Watson Pharmaceuticals, Inc, Corona, Calif.; and Dexferrum®; American Regent Inc., Shirley, N.Y.; both 100 mg/ml in 2 ml vials) were used.

For each experiment, all agents at all experimental concentrations were examined on the same day. For each concentration of iron agent, an equimolar stock solution was prepared on the day of use, using successive dilutions ($\leq 1:10$) in 0.9% NaCl.

Experimental Iron Concentrations

We examined concentrations of iron formulations over a range expected to include the maximum plasma concentration of agent after intravenous push injection ($C_{max}$) of 125 mg ferric gluconate (1900 µg/dl; (anonymous 2001)), 100 mg iron sucrose (3,000 µg/dl (Danielson et al. 1996)) or 100 mg iron dextran (3,080 to 3,396 µg/dl, data on file, American Regent Inc., Shirley, N.Y.).

Determination of Transferrin Bound Iron

The method of Jacobs et al. was used to determine the amount or iron serum transferrin bound (Jacobs and Alexander 1990). 0.1 ml of stock iron formulation solutions were added to 1.5 ml of fresh pooled serum and incubated for 5 minutes. The samples were passed over a 2.0 g alumina column to absorb organic and drug-bound iron, the elutants collected and reconstituted to a total volume of 1.5 ml, and the final iron concentration was determined using a Hitachi 717 chemistry analyzer (Boehringer Mannheim Corporation; Indianapolis, Ind.). Hitachi-specified ferrozine reagents (Boehringer) were used, which included detergent, buffers of citric acid and thiourea, ascorbate, and ferrozine. Briefly, this is a non-proteinizing method in which detergent clarifies lipemic samples, buffers lower pH to <2.0 to free iron as $Fe^{3+}$ from transferrin, ascorbate reduces $Fe^{3+}$ to $Fe^{2+}$ and ferrozine reacts with $Fe^2+$ to form a colored complex measured spectophotometrically at 56 0 nm. From this result the value of a control (blank) sample (0.1 ml 0.9% NaCl plus 1.5 ml serum, no added iron agent) was subtracted from the experimental sample readings, and the result were recorded as the Δ Tf-bound iron (µg/dl).

Figure 1:
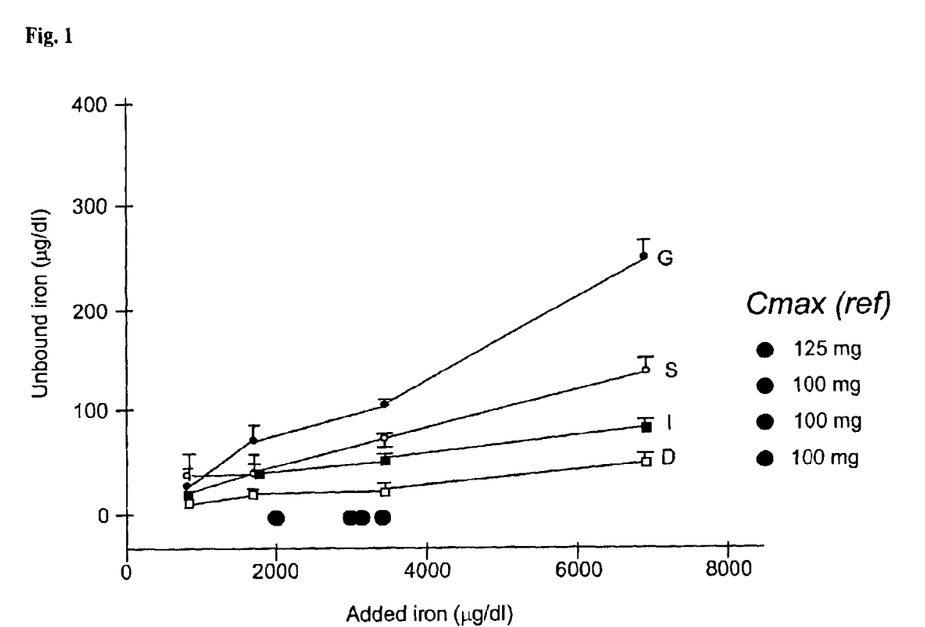
FIG. 1 shows the change in serum transferrin-bound iron ($\Delta$ iron) of the intravenous injection preparations for ferric gluconate (also known as sodium ferric gluconate complex in sucrose or Ferrlecit®; Watson Pharma, Inc.; Corona, Calif.), iron sucrose (Venofer® (iron sucrose injection USP); American Regent Inc.; Shirley, N.Y.), iron dextran (INFeD®; Watson Pharma, Inc.), and another iron dextran (Dexferrum®; American Regent Inc.) as related to the amount of added iron. x-axis, added elemental iron ($\mu$g/dl); $\gamma$-axis, $\Delta$ iron ($\mu$g/dl).

The following results were observed, and are represented below in Table 2 and graphically in FIG. 1 (x-axis, added elemental iron (µg/dl); y-axis, Δ iron (µg/dl); G, gluconate; S, sucrose; D, dexferrum; I, INFeD):

(1) column extraction removed >99% of detectable iron in serum-free samples of all intravenous iron agents;

(2) Δ iron increased as the dose of each added agent increased; and (3) Δ iron response differed in a dose-related manner among the four agents.

TABLE 2

| Conc | Ferrlecit® | | Venifer® | | Dexferrum® | | INFeD® | |
|---|---|---|---|---|---|---|---|---|
| µg/dl | Δ-G | Frx-G | Δ-S | Frx-S | Δ-D | Frx-D | Δ-I | Frx-I |
| 859 | 58.0 | 0.068 | 88.8 | 0.103 | 64.0 | 0.075 | 74.7 | 0.087 |
| 1719 | 124.5 | 0.072 | 105.7 | 0.061 | 66.5 | 0.039 | 79.0 | 0.046 |
| 3438 | 177.3 | 0.052 | 142.7 | 0.041 | 69.5 | 0.020 | 113.5 | 0.033 |
| 6875 | 339.0 | 0.049 | 229.5 | 0.033 | 99.0 | 0.014 | 172.0 | 0.025 |

Example 2

Tests to Diagnose and Evaluate RLS Symptoms and Monitor Treatment

The following tests are provided to aid in the evaluation of RLS diagnosis and treatment. Medical practitioners will select those tests that are appropriate for each particular patient. In many cases, monitoring for the diagnostic criteria for RLS will be sufficient to assess treatment efficacy.

Diagnostic factors

RLS is indicated when four diagnostic criteria are met: (1) a sensation of an urge to move the limbs (usually the legs); (2) motor restlessness to reduce sensations; (3) when at rest, symptoms return or worsen; and (4) marked circadian variation in occurrence or severity of RLS symptoms; that is, symptoms worsen in the evening and night (Allen and Earley 2001a).

The Johns Hopkins RLS Severity Scale (JHRLSS) (Allen and Earley 2001b)

This four point scale (0–3, corresponding to no symptom s to severe) is based on the time of day that RLS symptoms usually occur. Severity based on this scale can be derived from structured diagnostic clinical interviews (see below); this scale is most often used for characterization, not as a measure of treatment outcome.

Structured Diagnostic Clinical Interviews and Diagnostic Questionnaires

These are standardized, validated instruments are used to characterize RLS symptomatology administered by trained personnel or patients (self-administered). The forms and questions that may be asked of a potential RLS patient are referred to in Table 3.

TABLE 3

Structured diagnostic clinical interviews and diagnostic questionnaires

RLS Quality of life instrument (RLS-QLI, RLS Foundation May 1, 2002)
IRLSSG Restless legs syndrome rating scale
SF-12 health survey
Fatigue severity scale
Epworth sleepiness scale Sleep-RLS Log (Earley et al. 1998) This log is kept by RLS patients and record when RLS symptoms and sleep occur during the time periods requested by the clinician.

CNS and Blood Iron Status Sampling (Lumbar Puncture and Blood Sample Methods)

Lumbar puncture is done between L4/L5 or L5/S1 lumbar interspace using sterile technique. Ten mls of CSF are collected in 1 ml aliquots. From these samples, iron, ferritin ceruloplasm and transferrin concentrations are determined using standard techniques.

At the time of lumbar puncture, 10 mls of blood are also taken. The serum is then used to determine iron, ferritin, total iron binding capacity (TIBC), percentage iron saturation (% Sat) and transferrin receptor concentration. These variables are the most accurate blood indices for determining total body iron stores.

For many patients, blood sampling may be sufficient for monitoring treatment success and is desirable, given the risks that are involved in lumbar punctures.

Polysomnogram (PSG)

Night PSGs provide a direct measurement of sleep efficiency and the number of PLMS per hour of NREM sleep. Both of these measurements can be used to as primary dependent measures of severity. Sleep can also be scored visually according to the Rechtschaffen and Kales criteria (Rechtschaffen and Kales 1968), and PLMS can be scored using accepted standards (Force 1993).

Full standard clinical polysomnograms are obtained for two consecutive nights following methods well known in the art (Montplaisir et al. 1998). Hours that are usually monitored are 23:00 to 07:00.

Suggested Immobilization Test (SIT) (Montplaisir et al. 1986, Pelletier et al. 1992, Montplaisir et al. 1998)

The subject lies with the legs out and the upper body at a 60° incline. Subjects are monitored by EEG to prevent them from falling asleep, and EMG over the anterior tibial muscle to record leg movements. Subjects are requested not to move for one hour. During this period, movement will occur, and the number of movements correlate to RLS severity. Hours that are usually monitored are 08:00–09:00, 16:00–17:00 and 22:00–23:00.

Leg Activity Meters/Monitors (LAM)

Ambulatory recordings of leg activity can be obtained with the LAM. The LAM determines PLMS/hr with an error of ±5% compared to PSGs for patients with insomnia or PLMS (Gorny et al. 1986). The LAMs are habitually worn for at least 3 consecutive nights for each arbitrary period that the clinician would like to evaluate.

MRI Measurements of Brain Iron (Allen et al. 2001)

Briefly, multi-slice measurements of the relaxation rates $R_2^*$ and $R_2$ are obtained from a single scan using the gradient-echo sampling of FID and echo (GESFIDE) sequence on a GE 1.5T Signa System (General Electric, Milwaukee, Wis.), following known procedures (Gelman et al. 1999).

$R_2^*$ and $R_2$ images are reconstructed as a single, multi-slice "stack" in NIH Image 1.61, public domain NIH Image program (developed at the U.S. National Institutes of Health and available from the Institute). The slices showing the iron-containing structures on the $R_2^*$ images are displayed. The structures are then manually traced independently by two trained investigators, using standard anatomic guidelines for the slice with the best presentation of the area. Relaxation rates are averaged for both left and right hemispheres. $R_2'$ is then calculated from the difference of $R_2^*$ and $R_2$.

Example 3

Venofer® and other Iron Complexes Administration (Prophetic)

Dosage of Venofer® may be adjusted by a medical professional according to body weight, disease severity, and each patients' individual response to the medication. Intravenous administration of Venofer® or other iron complexes are given as in Table 4.

For example, a 1000 mg of Venofer® is given as a single intravenous dose to RLS patients. A single intravenous treatment will provide relief from RLS symptoms for an extended period of time, approximately 2–12 months, although relief may be granted for shorter or longer periods. If desired, post-infusion changes in CNS iron status can be monitored using CNS and blood iron tests (see Example 2). Post-infusion changes in RLS are assessed using standard subjective (patient diary, rating scale) as well as objective (P50, SIT, Leg Activity Meters, see Example 2) measures of clinical status. If desired, to better evaluate RLS symptom amelioration, CSF and serum iron values are determined, as well as those for brain iron, and full clinical evaluations with sleep and immobilization tests are obtained prior to treatment, approximately two weeks after treatment, and again 12 months later or when symptoms return.

Prior to administration, Venofer® [supplied as 100 mg elemental iron in 5 ml (20 mg/ml] is diluted in normal saline to 2–5 mg/ml. The solution is then administered through a free-flowing peripheral or central intravenous infusion. The volume of the pharmaceutical solution is based on the safe volume for the individual patient, as determined by a medical professional.

For direct injection, 100 mg may be administered over 2 minutes and 200 mg over 5 minutes. The injection is repeated a week later, or as necessary upon the recurrence of RLS symptoms.

TABLE 4

Examples of administration of Venofer ® to RLS patients

| Venofer ® doses (elemental iron, mg) | Time administered intravenously | Repetition | Total dose (elemental iron, mg) |
|---|---|---|---|
| (1) 500 (2) 250 | during 4 hours | (A) within 1 week of symptoms have not abated; OR, (B) upon the recurrence of RLS symptoms | (A) (1) 1000 (2) 500 (B) (1) 500 (2) 250 |
| (1) 500 (2) 250 | slow infusion during 4 hours | Repeat within 4 to 7 days | (1) 1,000 (2) 500 |
| (1) 1,000 (2) 500 (3) 250 (4) 100 | slow infusion over 4–6 hours | Upon the recurrence of RLS symptoms | (1) 1,000 (2) 500 (3) 250 (4) 100 |

References

Allen R P, Barker P B, Wehrl F, Song H K, Earley C J. (2001) MRI measurement of brain iron in patients with restless legs syndrome. *Neurology* 56: 263–265

Allen R P, Earley C J. (1996) Augmentation of the restless legs syndrome with carbidopa/levodopa. *Sleep* 19: 205-213

Allen R P, Earley C J. (2001a) Restless legs syndrome: a review of clinical and pathophysiologic features. *J Clin Neurophysiol* 18: 128–147

Allen R P, Earley C J. (2001b) Validation of the Johns Hopkins restless legs severity scale. *Sleep Medicine* 2: 239–242

Anonymous, (2001) Ferrelecit insert; Revision 02/01.

Andreasen H B, Christensen L, (2001) Iron-dextran compound for use as a component in a therapeutical Composition for prophylaxis or treatment of iron-deficiency. Pharmacosmos Holding A/S Ben-Shachar D, Finberg J P, Youdim M B. (1985) Effect of iron chelators on dopamine D2 receptors. *J Neurochem* 45: 999–1005

Breuer W, Cabantchik Z I. (2001) A fluorescence-based one-step assay for serum non-transferrin-bound iron. *Anal Biochem* 299: 194–202

Chesson A L Jr, Wise M, Davila D, Johnson S, Littner M, Anderson W M, Hartse K, Rafecas J. (1999) Practice parameters for the treatment of restless legs syndrome and periodic limb movement disorder. An American Academy of Sleep Medicine Report. Standards of Practice Committee of the American Academy of Sleep Medicine. *Sleep* 22: 961–968

Conrad M E, Umbreit J N, Moore E G. (1999) Iron absorption and transport. *Am J Med Sci* 318: 213–229

Cooper J, Bloom F, Roth R, (1991) The biochemical basis of neuropharmacology. Oxford Universty Press, New York, N.Y.

Danielson B G, Salmonson T, Derendorf H, Geisser P. (1996) Pharmacokinetics of iron(III)-hydroxide sucrose complex after a single intravenous dose in healthy volunteers. *Arzneimittelforschung* 46: 615–21

Earley C J, Allen R P. (1996) Pergolide and carbidopa/levodopa treatment of the restless legs syndrome and periodic leg movements in sleep in a consecutive series of patients. *Sleep* 19: 801–810

Earley C J, Connor J R, Beard J L, Malecki E A, Epstein D K, Allen R P. (2000) Abnormalities in CSF concentrations of ferritin and transferrin in restless legs syndrome. *Neurology* 54: 1698–700

Earley C J, Yaffee J B, Allen R P. (1998) Randomized, double-blind, placebo-controlled trial of pergolide in restless legs syndrome. *Neurology* 51: 1599–602

Ekbom K. (1960) Restless legs syndrome. *Neurology* 10: 868–873

Esposito B P, Breuer W, Slotki I, Cabantchik Z I. (2002) Labile iron in parenteral iron formulations and its potential for generating plasma nontransferrin-bound iron in dialysis patients. *Eur J Clin Invest* 32 Suppl 1: 42–9

Erikson K M, Jones B C, Beard J L. (2000) Iron deficiency alters dopamine transporter functioning in rat striatum. *J Nutr* 130: 2831–2837

Fishbane S, Ungureanu V D, Maesaka J K, Kaupke C J, Lim V, Wish J. (1996) The safety of intravenous iron dextran in hemodialysis patients. *Am J Kidney Dis* 28: 529–534

Geisser P, Baer M, Schaub E. (1992) Structure/histotoxicity relationship of parenteral iron preparations. *Arzneimittelforschung* 42: 1439–1452

Gelman N, Gorell J M, Barker P B, Savage R M, Spickler E M, Windham J P, Knight R A. (1999) MR imaging of human brain at 3.0 T: preliminary report on transverse relaxation rates and relation to estimated iron content. *Radiology* 210: 759–767

Gennaro A, (2000) Remington: the science and practice of pharmacy. Lippincott Williams & Wilkins, Baltimore, Md.

Gorny S, Allen R, Krasuman D, Earley C. (1986) Evaluation of the PAM-RL system for the detection of periodic leg movements during sleep in the lab and home environments. *Sleep* 21 (Suppl)183

Groman E, Josephson L, (1990) Low molecular weight carbohydrates as additives to stabilize metal oxide compositions.

Groman, E V, Josephson, L, Lewis, J M, (1989) Biologically degradable superparamagnetic materials for use in clinical applications.

Hamstra R D, Block M H, Schocket A L. (1980) Intravenous iron dextran in clinical medicine. *JAMA* 243: 1726–1731

Hening W A, Walters A, Kavey N, Gidro-Frank S, Cote L, Fahn S. (1986) Dyskinesias while awake and periodic movements in sleep in restless legs syndrome: treatment with opioids. *Neurology* 36: 1363–6

Hening W, Allen R, Earley C, Kushida C, Picchietti D, Silber M. (1999) The treatment of restless legs syndrome and periodic limb movement disorder. An American Academy of Sleep Medicine Review. *Sleep* 22: 970–999

Jacobs J C, Alexander N M. (1990) Colorimetry and constant-potential coulometry determinations of transferrin-bound iron, total iron-binding capacity, and total iron in serum containing iron-dextran, with use of sodium dithionite and alumina columns. *Clin Chem* 36: 1803–1807

Montplaisir J, Boucher S, Nicolas A, Lesperance P, Gosselin A, Rompre P, Lavigne G. (1998) Immobilization tests and periodic leg movements in sleep for the diagnosis of restless leg syndrome. *Mov Disord* 13: 324–329

Montplaisir J, Godbout R, Poirier G, Bedard M A. (1986) Restless legs syndrome and periodic movements in sleep: physiopathology and treatment with L-dopa. *Clin Neuropharmacol* 9: 456–463

Montplaisir J, Lorrain D, Godbout R. (1991) Restless legs syndrome and periodic leg movements in sleep: the primary role of dopaminergic mechanism. *Eur Neurol* 31: 41–43

Nelson C, Erikson K, Pinero D J, Beard J L. (1997) In vivo dopamine metabolism is altered in iron-deficient anemic rats. *J Nutr* 127: 2282–2288

Nordlander N. (1953) Therapy in restless legs. *Acta Med Scand* 145457

O'Keeffe S T, Gavin K, Lavan J N. (1994) Iron status and restless legs syndrome in the elderly. *Age Ageing* 23: 200–203

Pelletier G, Lorrain D, Montplaisir J. (1992) Sensory and motor components of the restless legs syndrome. *Neurology* 42: 1663–1666

Pollmacher T, Schulz H. (1993) Periodic leg movements (PLM): their relationship to sleep stages. *Sleep* 16: 572–577

Rechtschaffen A, Kales A, (1968) A manual of standardized terminology, techniques and scoring system for sleep stages of human subjects. US Dept. of Health, Education and Welfare, Public HealthServices, Bethesda, Md.

Silber M H, Shepard J W Jr, Wisbey J A. (1997) Pergolide in the management of restless legs syndrome: an extended study. *Sleep* 20: 878–82

Staedt J, Stoppe G, Kogler A, Riemann H, Hajak G, Munz D L, Emrich D, Ruther E. (1995) Nocturnal myoclonus syndrome (periodic movements in sleep) related to central dopamine D2-receptor alteration. *Eur Arch Psychiatry Clin Neurosci* 245: 8–10

Sun E R, Chen C A, Ho G, Earley C J, Allen R P. (1998) Iron and the restless legs syndrome. *Sleep* 21: 371–377

Force T A. (1993) Recording and scoring leg movements. *Sleep* 16: 748–759

Turjanski N, Lees A J, Brooks D J. (1999) Striatal dopaminergic function in restless legs syndrome: 18F-dopa and 11C-raclopride PET studies. *Neurology* 52: 932–937

Ward R J, Dexter D, Florence A, Aouad F, Hider R, Jenner P, Crichton R R. (1995) Brain iron in the ferrocene-loaded rat: its chelation and influence on dopamine metabolism. *Biochem Pharmacol* 49: 1821–1826

What is claimed is:

1. A method of treating Restless Leg Syndrome, comprising administering to a subject an iron sucrose having an iron release rate greater than IDI, wherein the iron release rate is determined at a concentration of at least 2,000 µg/dl.

2. The method of claim 1, wherein the administering is parenterally.

3. The method of claim 1, wherein an amount of iron administered is 100 mg–2000 mg.

4. The method of claim 1, further comprising a second administration of said iron complex upon recurrence of at least one symptom of Restless Leg Syndrome.

5. The method of claim 1, further comprising a second administration of said iron complex after 4 days–12 months after the first administration.

6. The method of claim 1, wherein the iron sucrose is iron sucrose injection USP.

7. A method of treating Restless Leg Syndrome, comprising administering to a subject an iron sucrose having an iron release rate of at least 115 µg/dl at a concentration of 3438 µg/dl by the alumina column test.

8. The method of claim 7, wherein the release rate is at least 120 µg/dl.

9. The method of claim 7, wherein the release rate is at least 140 µg/dl.

10. The method of claim 7, wherein the administering is intravenous.

11. The method of claim 7, wherein an amount of iron administered is 100 mg–2000 mg.

12. The method of claim 7, further comprising a second administration of said iron complex upon recurrence of at least symptom of Restless Leg Syndrome.

13. The method of claim 7, further comprising a second administration of said iron complex after 4 days–12 months after the first administration.

14. The method of claim 8, wherein an amount of iron is 100 mg–2000 mg.

15. The method of claim 9, wherein an amount of iron is 100 mg–2000 mg.

16. A kit, comprising:

an iron sucrose composition having a release rate greater than IDI, a syringe, and a needle for the syringe, wherein the iron release rare is determined at a concentration of at least 2,000 µg/dl.

* * * * *